(12) United States Patent
Bullard

(10) Patent No.: US 10,898,343 B2
(45) Date of Patent: Jan. 26, 2021

(54) MULTI-LAYER OSTEOINDUCTIVE, OSTEOGENIC, AND OSTEOCONDUCTIVE CARRIER

(71) Applicant: Bullard Spine, LLC, Raleigh, NC (US)

(72) Inventor: Dennis E. Bullard, Raleigh, NC (US)

(73) Assignee: Bullard Spine, LLC, Raleigh, NC (US)

( * ) Notice: Subject to any disclaimer, the term of this patent is extended or adjusted under 35 U.S.C. 154(b) by 196 days.

(21) Appl. No.: 16/158,553

(22) Filed: Oct. 12, 2018

(65) Prior Publication Data

US 2019/0046332 A1  Feb. 14, 2019

Related U.S. Application Data

(63) Continuation of application No. 15/226,686, filed on Aug. 2, 2016, now Pat. No. 10,105,237, which is a
(Continued)

(51) Int. Cl.
*A61F 2/44* (2006.01)
*A61L 27/54* (2006.01)
(Continued)

(52) U.S. Cl.
CPC ........ *A61F 2/4455* (2013.01); *A61B 17/7049* (2013.01); *A61L 27/54* (2013.01); *A61L 27/56* (2013.01); *A61L 27/58* (2013.01); *A61B 17/7001* (2013.01); *A61B 2017/00004* (2013.01); *A61F 2002/30062* (2013.01); *A61F 2002/30072* (2013.01); *A61F 2002/30537* (2013.01); *A61F 2002/30622* (2013.01);
(Continued)

(58) Field of Classification Search
CPC ...... A61B 17/70; A61B 17/7049–7052; A61B 17/7061–707; A61F 2/44; A61F 2/4455; A61F 2002/4495; A61F 2002/4445–445; A61F 2002/3006–30064
See application file for complete search history.

(56) References Cited

U.S. PATENT DOCUMENTS 4,566,262 A * 1/1986 Schmucker ............ D02G 1/082
57/264
5,084,051 A * 1/1992 Tormala .................. A61L 27/10
606/77
(Continued)

*Primary Examiner* — Eduardo C Robert
*Assistant Examiner* — Michelle C Eckman
(74) *Attorney, Agent, or Firm* — Troutman Pepper Hamilton Sanders LLP; James E. Schutz; Chris Davis

(57) ABSTRACT

A spinal stabilization system for use in a vertebral column of a patient, comprising: a multi-layer osteogenic carrier device comprising: a delivery layer comprising a porous material and an osteogenic material; and a support layer in communication with the delivery layer, the support layer capable of substantially conforming to an anatomical feature in the vertebral column of the patient, wherein the support layer holds the delivery layer in proximity to the anatomical feature; at least one rod; at least one rod clip; and at least one fastener are disclosed. The multi-layer osteogenic carrier device can further comprise an adhesive layer capable of adhering the carrier to at least a portion of an anatomical feature, the adhesive layer in communication with at least a portion of the delivery layer.

17 Claims, 6 Drawing Sheets

Related U.S. Application Data continuation of application No. 12/778,723, filed on May 12, 2010, now Pat. No. 9,439,685.

(60) Provisional application No. 61/177,323, filed on May 12, 2009.

(51) Int. Cl.
| | | |
|---|---|---|
| *A61L 27/56* | (2006.01) | |
| *A61L 27/58* | (2006.01) | |
| *A61B 17/70* | (2006.01) | |
| *A61B 17/00* | (2006.01) | |
| *A61F 2/30* | (2006.01) | |

(52) U.S. Cl.
CPC .............. *A61F 2310/00976* (2013.01); *A61L 2300/412* (2013.01); *A61L 2300/608* (2013.01); *A61L 2430/02* (2013.01)

(56) References Cited

U.S. PATENT DOCUMENTS

| | | | | |
|---|---|---|---|---|
| 5,676,699 | A * | 10/1997 | Gogolewski | C08L 89/00 623/16.11 |
| 6,294,041 | B1 * | 9/2001 | Boyce | A61L 27/3608 156/275.5 |
| 6,350,284 | B1 * | 2/2002 | Tormala | A61F 2/2846 623/17.19 |
| 6,409,764 | B1 * | 6/2002 | White | A61L 27/54 623/16.11 |
| 6,613,091 | B1 | 9/2003 | Zdeblick et al. | |
| 6,719,795 | B1 * | 4/2004 | Cornwall | A61B 17/707 606/246 |
| 7,261,734 | B2 * | 8/2007 | Gellman | A61L 27/34 623/1.42 |
| 7,722,895 | B1 * | 5/2010 | McKay | A61L 27/227 424/423 |
| 7,731,756 | B2 * | 6/2010 | Maspero | A61L 27/3847 433/201.1 |
| 7,806,911 | B2 * | 10/2010 | Peckham | A61B 17/7059 606/248 |
| 7,824,699 | B2 * | 11/2010 | Ralph | A61K 9/0024 424/422 |
| 8,182,511 | B2 * | 5/2012 | Henderson | A61B 17/7055 606/246 |
| 8,231,624 | B1 * | 7/2012 | Strippgen | A61B 17/826 606/70 |
| 8,470,354 | B2 | 6/2013 | McKay et al. | |
| 8,518,123 | B2 * | 8/2013 | Jensen | A61L 27/44 623/23.51 |
| 8,702,808 | B2 * | 4/2014 | Teoh | A61L 27/56 623/23.61 |
| 9,827,023 | B2 * | 11/2017 | Henderson, Sr. | A61B 17/7059 |
| 2002/0143403 | A1 * | 10/2002 | Vaidyanathan | A61L 27/446 623/23.51 |
| 2003/0093154 | A1 | 5/2003 | Estes et al. | |
| 2004/0049270 | A1 * | 3/2004 | Gewirtz | A61F 2/28 623/17.11 |
| 2004/0082998 | A1 * | 4/2004 | Shinomiya | A61L 27/56 623/17.11 |
| 2004/0087955 | A1 * | 5/2004 | Bordi | A61B 17/8085 606/74 |
| 2004/0225360 | A1 * | 11/2004 | Malone | A61B 17/8685 623/17.11 |
| 2004/0259972 | A1 * | 12/2004 | Ringeisen | A61F 2/0059 523/113 |
| 2006/0004358 | A1 * | 1/2006 | Serhan | A61B 17/70 606/281 |
| 2006/0264948 | A1 * | 11/2006 | Williams | A61B 17/8085 606/71 |
| 2007/0142916 | A1 * | 6/2007 | Olson, Jr. | C08L 89/06 623/17.11 |
| 2007/0260324 | A1 * | 11/2007 | Joshi | A61F 2/4465 623/23.51 |
| 2007/0270844 | A1 * | 11/2007 | Lin | A61F 2/4455 606/279 |
| 2007/0272259 | A1 * | 11/2007 | Allard | A61B 17/7065 128/898 |
| 2007/0288014 | A1 * | 12/2007 | Shadduck | A61B 17/68 606/279 |
| 2008/0004702 | A1 * | 1/2008 | Denoziere | A61F 2/4405 623/17.13 |
| 2008/0004714 | A1 * | 1/2008 | Lieberman | A61F 2/00 623/23.76 |
| 2008/0033429 | A1 * | 2/2008 | Harlow | A61K 9/0024 606/53 |
| 2008/0065218 | A1 * | 3/2008 | O'Neil | A61F 2/442 623/17.16 |
| 2008/0103596 | A1 * | 5/2008 | Shikinami | A61F 2/442 623/17.16 |
| 2008/0147098 | A1 * | 6/2008 | Trieu | A61F 2/442 606/151 |
| 2008/0154376 | A1 * | 6/2008 | Bergeron | A61F 2/442 623/17.16 |
| 2008/0174043 | A1 * | 7/2008 | Denoziere | A61F 2/3094 264/232 |
| 2008/0195211 | A1 * | 8/2008 | Lin | A61F 2/30942 623/17.16 |
| 2008/0220045 | A1 | 9/2008 | Shalaby et al. | |
| 2008/0234766 | A1 * | 9/2008 | Henderson | A61B 17/8891 606/86 B |
| 2008/0269756 | A1 * | 10/2008 | Tomko | A61B 17/1757 606/87 |
| 2009/0005882 | A1 * | 1/2009 | Boyer, III | A61F 2/28 623/23.63 |
| 2009/0018584 | A1 * | 1/2009 | Henderson, Sr. | A61B 17/7055 606/246 |
| 2009/0043394 | A1 * | 2/2009 | Zdeblick | A61L 27/227 623/17.16 |
| 2009/0048677 | A1 * | 2/2009 | McLeod | A61F 2/442 623/17.16 |
| 2009/0177230 | A1 * | 7/2009 | Henderson, Sr. | A61B 17/7055 606/246 |
| 2009/0240337 | A1 * | 9/2009 | Myung | A61L 33/0094 623/18.11 |
| 2009/0317447 | A1 * | 12/2009 | Hsiao | A61F 2/28 424/426 |
| 2010/0009103 | A1 * | 1/2010 | Kuboki | A61L 27/32 428/34.6 |
| 2010/0057114 | A1 * | 3/2010 | Butler | A61B 17/7062 606/151 |
| 2010/0152575 | A1 * | 6/2010 | Henderson | A61B 17/7055 600/425 |
| 2010/0160964 | A1 * | 6/2010 | Malek | A61F 2/4455 606/246 |
| 2010/0266660 | A1 | 10/2010 | McKay et al. | |
| 2010/0268337 | A1 * | 10/2010 | Gordon | B29C 44/00 623/16.11 |
| 2010/0292734 | A1 * | 11/2010 | Bullard | A61F 2/4455 606/246 |
| 2010/0305689 | A1 * | 12/2010 | Venkatraman | C08L 67/04 623/1.46 |
| 2011/0034975 | A1 * | 2/2011 | Ferree | A61B 17/742 607/105 |
| 2011/0313323 | A1 * | 12/2011 | Henderson | A61B 17/7055 600/594 |
| 2012/0083882 | A1 * | 4/2012 | Shih | A61B 17/8085 623/17.11 |
| 2012/0209339 | A1 * | 8/2012 | Scodary | A61B 17/7071 606/86 R |
| 2012/0215260 | A1 * | 8/2012 | Paul | A61F 2/4405 606/249 |
| 2013/0138222 | A1 * | 5/2013 | Horton | A61F 2/28 623/23.61 |
| 2013/0144386 | A1 * | 6/2013 | Horton | A61K 35/50 623/17.11 |
| 2013/0184826 | A1 * | 7/2013 | Thaiyananthan | A61B 17/7062 623/17.16 |

(56) References Cited

U.S. PATENT DOCUMENTS

| | | | |
|---|---|---|---|
| 2013/0226271 A1* | 8/2013 | Ferree | A61F 7/12 607/96 |
| 2013/0304129 A1* | 11/2013 | Hawkins | A61B 17/7056 606/276 |
| 2014/0052183 A1* | 2/2014 | Freese | A61B 17/0401 606/248 |
| 2014/0277569 A1* | 9/2014 | Lange | A61F 2/28 623/23.51 |
| 2015/0018969 A1* | 1/2015 | Fulmer | A61F 2/07 623/23.76 |
| 2015/0080951 A1* | 3/2015 | Yeh | A61B 17/707 606/249 |
| 2015/0257789 A1* | 9/2015 | Squires | A61B 17/7071 606/246 |
| 2015/0265407 A1* | 9/2015 | Horvath | A61F 2/2803 623/16.11 |
| 2015/0282944 A1* | 10/2015 | Guizzardi | A61F 2/442 623/17.16 |
| 2015/0289979 A1* | 10/2015 | Gabele | A61L 27/042 623/23.55 |
| 2015/0374412 A1* | 12/2015 | Walsh | A61B 17/7062 606/249 |
| 2016/0074166 A1* | 3/2016 | Coale | A61L 27/047 623/23.53 |
| 2016/0151539 A1* | 6/2016 | Anderson | A61L 27/365 623/23.5 |
| 2016/0213403 A1* | 7/2016 | Bowden | A61B 17/70 |
| 2017/0027621 A1* | 2/2017 | Shenoy | A61F 2/44 |
| 2017/0196508 A1* | 7/2017 | Hunter | A61B 5/036 |
| 2017/0281250 A1* | 10/2017 | Lange | A61B 17/7097 |
| 2017/0296239 A1* | 10/2017 | Cordaro | A61B 17/7059 |
| 2017/0304073 A1* | 10/2017 | Pedoulias | A61B 17/68 |
| 2017/0325851 A1* | 11/2017 | Acosta | A61B 17/7062 |
| 2017/0325852 A1* | 11/2017 | Chen | A61B 17/70 |
| 2018/0185065 A1* | 7/2018 | McNally | A61B 34/10 |
| 2018/0256353 A1* | 9/2018 | Nyahay | A61F 2/4455 |

\* cited by examiner

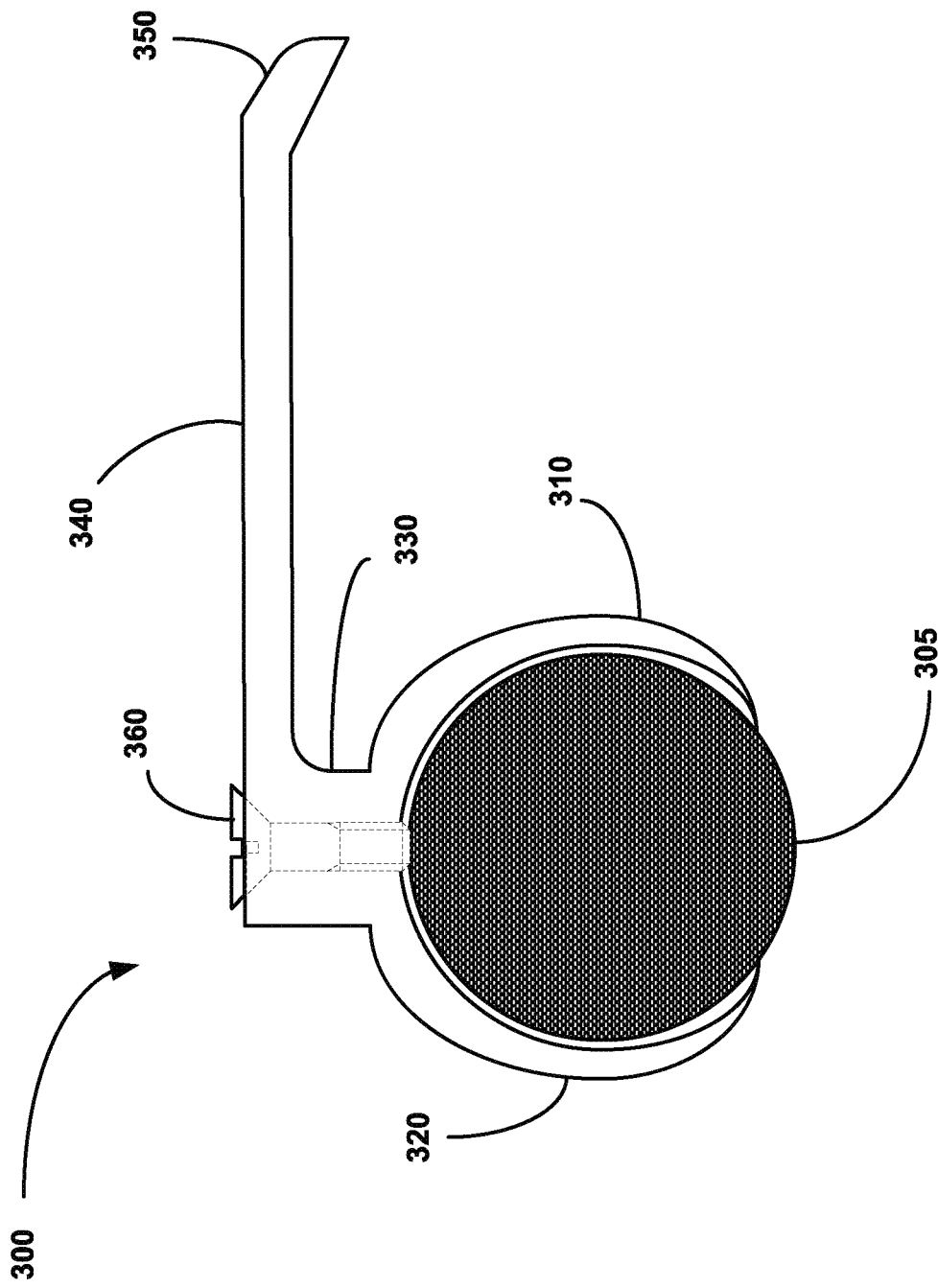

MULTI-LAYER OSTEOINDUCTIVE, OSTEOGENIC, AND OSTEOCONDUCTIVE CARRIER

CROSS-REFERENCE TO RELATED APPLICATION

This Application is a continuation of U.S. patent application Ser. No. 15/226,686 (now U.S. Pat. No. 10,105,237), filed on Aug. 2, 2016, which is a continuation of U.S. patent application Ser. No. 12/778,723 (now U.S. Pat. No. 9,439,685), filed on May 12, 2010, and claims priority to U.S. Provisional Patent Application No. 61/177,323 filed on May 12, 2009, all of which are hereby incorporated in their entirety as if fully set forth herein.

TECHNICAL FIELD

Embodiments of the present invention relate to implantable osteogenesis systems, devices, and methods for their use, and particularly to systems, methods, and devices that facilitate application of an osteogenic/osteoinductive/osteoconductive substance to vertebrae in the lumbar, thoracic, and cervical spine.

BACKGROUND

Fusion of spinal vertebrae is often necessary to relieve debilitating pain or correct a deformity. Lumbar, thoracic and cervical spinal fusions are often prescribed for patients suffering from degenerative disk disease (whose symptoms include neck, chest, or back pain of discogenic or spondylotic origin with degeneration of the disk or surrounding structures confirmed by patient history and radiographic studies), trauma (including fractures), tumors, deformity (indicated by kyphosis, lordosis, or scoliosis) pseudoarthrosis, and/or failed previous fusions.

Spinal surgical fusion is the process of bringing together two or more vertebrae under conditions whereby the vertebrae fuse together to form a unitary member of the spinal column. When vertebrae are fused, e.g., with bone grafts, graft extenders, or interbody spacers such as interbody cages or boxes (collectively termed "grafts" herein), it is desirable to stabilize the fused vertebrae using apparati such as plates, cages, or screws to fixate one or more lumbar, thoracic, or cervical vertebra to another to promote fusion across motion segments. In carrying out the procedure, the members must be brought together under conditions that are critically controlled to prevent infection, maintain alignment of opposing members, and allow for the stress in the bone that is generated as the healing process matures. Immobilization is an important requirement during this healing process.

In addition to stabilization, osteogenic, osteoconductive and/or osteoinductive substances are often applied to surrounding areas to promote bone growth. An example of such a substance is the Trinity™ multipotential cellular bone matrix which has osteogenic, osteoconductive and/or osteoinductive properties. The Trinity™ matrix consists of viable adult stem cells, which are osteogenic cells. The Trinity™ matrix also has osteoinductive signals and provides an osteoconductive matrix which can be used in a wide variety of surgical applications where filling a bone void or stimulating bone growth is required. The Trinity™ matrix is but one osteogenic substance on the market and is mentioned for exemplary purposes only. Much like an autograft, the Trinity™ matrix has the three key bone growth properties: osteogenic cells, osteoinductive signals, and an osteoconductive scaffold, but other products currently on the market and many that are in development may prove to be as good or even better using similar or newer biologic principles. The device described is designed to have the flexibility to be used by multiple types of biologic products.

A universal problem with the use of osteogenic biologics is handling. The substances come in prepacked sizes and amounts. Therefore, it is difficult to obtain the exact amount of the substances actually needed, and a surgeon will often find himself/herself with either too much or too little. Given the relatively high cost of these substances, even a small amount of wasted material per patient becomes a major cost factor to patients, hospitals, and benefit providers. Another difficulty exists with the application and diffusion of the substance. The osteogenic substances are placed directly in the body in the area of surgical exposure where bone growth is desired. A considerable amount of the substance will consistently diffuse away from the initial site of application into the adjacent structures of the body, then be absorbed by surrounding muscle, or otherwise become dislodged or transplanted, and hence will be wasted and not produce the desired effect. Additionally, because the substances are not generally moldable and/or adherent and paste-like, it is difficult to apply them into small spaces, such as between vertebrae, and expect the substance to be retained in that area. Inevitably, when inserting the substance between vertebrae, a considerable amount is scraped off during insertion and remains on the outer surface of the vertebrae, rather than between them in the space to be fused.

The recent trend in spine surgery are minimally invasive surgical (MIS) techniques which seems to parallel the evolution of interventional vascular and cardiac technology, arthroscopy for joint disorders, and laparoscopic techniques for general and gynecologic procedures. This is true for lumbar fusions using MIS techniques, such as XLIF, TLIF, or PLIF approaches. Minimally invasive approaches to the spine are rapidly becoming more common and have many positive features including: shorter operating room times; less blood loss; less disruption of tissue; and shorter recovery times. One of the criticisms of the MIS has been that these techniques do not allow for incorporation of effective posterior-lateral graft material, such as a Trinity™ or other osteogenic, osteoconductive, and/or osteoinductive biologic materials. While the hardware for minimally invasive surgeries (MIS) is rapidly expanding, the optimal use of biologics in MIS has not been as actively pursued. Therefore, while smaller incisions reduce recovery time, the rate of vertebral fusion has been reported to also be reduced due to the absence of an optimal way to deliver proper graft material.

It is therefore an object of the present invention to provide a device, system, and method for the application of an osteogenic, osteoconductive and/or osteoinductive biologic material to target sites in the lumbar, thoracic and cervical spine.

BRIEF SUMMARY

Embodiments of the present invention are directed to a multi-layer osteogenic, osteoconductive, and osteoinductive carrier device or system for applying an osteogenic, osteoconductive and/or osteoinductive biologic material to target sites in the lumbar, thoracic and cervical spine. This system will allow the application of these types of substances to a bone surface, and methods for making and using said carrier or system. In an exemplary embodiment, the carrier can comprise three layers: a first thin absorbent layer, which is adherent, easily moldable, and osteoinductive; a second adherent layer, which has a longer time of absorption than the first layer, and which is both osteoinductive and osteoconductive and even potentially osteogenic; and a third layer, which is more rigid but molded or pliable, absorbs over a substantially longer time than the first and second layers, and is non-reactive.

An aspect of the present invention comprises a multi-layer osteogenic carrier device comprising: a delivery layer comprising a porous material and an osteogenic material; and a support layer in communication with the delivery layer, the support layer capable of substantially conforming to an anatomical feature, wherein the support layer can hold the delivery layer in proximity to the anatomical feature. In an exemplary embodiment, the porous material of the delivery layer defines a cavity and at least a portion of the osteogenic material is disposed in the cavity. The porous material can comprise an osteoconductive material, and an osteoinductive material can be disposed in the cavity. In the various embodiments of the present invention, a multi-layer osteogenic carrier device can further comprise an adhesive layer capable of adhering the carrier to at least a portion of an anatomical feature, the adhesive layer in communication with at least a portion of the delivery layer. The adhesive layer comprises an osteoinductive material.

In one embodiment, the porous material of the delivery layer comprises a first bioresorbable material having a first absorption rate in a body, and the support layer comprises a second bioresorbable material having a second absorption rate in a body, wherein the first absorption rate for the first bioresorbable material is greater than the absorption rate for the second bioresorbable material. In another embodiment, the adhesive layer comprises a first bioresorbable material having a first absorption rate, the porous material of the delivery layer comprises a second bioresorbable material having a second absorption rate in a body, and the support layer comprises a third bioresorbable material having a third absorption rate in a body, wherein the absorption rate for the first bioresorbable material is greater than the absorption rate for the second bioresorbable material and the absorption rate for the second bioresorbable material is greater than the absorption rate for the third bioresorbable material The first layer can be adherent to bone and/or tissue. The adhesive layer, also referred to as a first layer, can be adherent inherently or when activated by heat, fluid (such as sterile saline, blood, or serum), or by another activating agent. The adherent properties of the first layer enable the carrier to stick to the surface of the decorticated bone at the planned fusion site once positioned there by the surgeon. The first layer is also preferably moldable/pliable, and rapidly absorbable by the body. This allows the first layer to substantially conform to the contours of the decorticated bone for an even distribution over the optimal contact area. The first layer can also be infused/impregnated with or able to stimulate bone morphogenetic protein (BMP), an angiogenic factor, or another osteoinductive substance. Alternatively, the first layer itself can be osteoconductive and/or osteoinductive.

The second layer, also referred to as the delivery layer, can be osteoconductive and define a cavity adapted to receive an osteoinductive, osteogenic or osteoconductive substance. The substance can be inserted into the carrier through an open end, which can be sewn up or otherwise fastened or closed once the substance is inserted. Alternatively, osteoinductive, osteogenic or osteoconductive substances can be injected through a port or inlet in the carrier or the substance can be sealed within the carrier during manufacturing. The second layer can serve as the osteoconductive scaffolding for fusion but could also have additional osteoinductive, and/or osteogenic material to optimize the fusion.

The support layer, also referred to as the third layer, is preferably absorbed much slower than the first and second layers. While the third layer can be moldable, it is preferably sufficiently rigid once placed to keep the first and second layers in place and prevent them from becoming separated from the decorticated bone surface, and lost within the surrounding muscle and soft tissue where they would be absorbed without any beneficial effect. The third layer if it is in a separate wafer form could be cut to the appropriate size and shape needed then activated once it is placed in contact with the first and second layers and the bony anatomy.

The carrier and/or third layer can become activated when moistened, heated or otherwise altered making the layers moldable/pliable. This allows the surgeon to further compress the carrier to substantially conform to the surface contours of the bone. The carrier, with the osteoinductive, osteogenic and/or osteoconductive substance within the second layer, can be applied directly onto the decorticated bone where fusion is desired. Once activated, the first layer can be adherent and can keep the carrier in the position determined by the surgeon as well as stimulating the communication of cells and stimulatory agents between the decorticated bone and the potential fusion mass within the second layer. In an exemplary embodiment, the carrier can adopt a tubular shape. In another exemplary embodiment, the carrier is adapted for insertion between adjacent vertebrae.

Another aspect of the present invention comprises a system for applying the multi-layer osteogenic carrier to an anatomical surface, the system comprising: a multi-layer osteogenic carrier device comprising: a delivery layer comprising a porous material and an osteogenic material; and a support layer in communication with the delivery layer, the support layer capable of substantially conforming to an anatomical feature, wherein the support layer can hold the delivery layer in proximity to the anatomical feature; and a spinal stabilization system comprising at least one rod; and a rod clip comprising: a first leg and a second leg, the legs adapted to attach to a rod; and an arm connected to the legs by a stem, the arm configured to extend from the spinal stabilization system, wherein the arm of rod clip is positioned to apply a pressure to the support layer of the multi-layer osteogenic carrier device so as to hold the multi-layer osteogenic carrier device in proximity to an anatomical feature.

In an exemplary embodiment, the system can comprise a rod clip adapted to maintain pressure on the third layer of the device/carrier and prevent the carrier from drifting away from the fusion site. The clip can comprise two curved legs adapted to snap onto a rod of a spinal stabilization structure. The legs can by connected to an arm by a stem. The arm can extend from the stabilization system to engage the third layer of the carrier. A fastener, such as a screw or bolt, can be inserted through the stem to lock the clip onto the rod once it has been placed in the desired position relative to the carrier. As such, the system can comprise a plurality of rod clips and a plurality of multi-layer osteogenic carrier devices. The system can further comprise a fastener, the fastener inserted through the stem to lock the rod clip onto the rod once the rod clip has been placed in the desired position relative to the multi-layer osteogenic carrier.

Another aspect of the present invention comprises a spinal stabilization system for use in a vertebral column of a patient, comprising: a multi-layer osteogenic carrier device comprising: a delivery layer comprising a porous material and an osteogenic material; and a support layer in communication with the delivery layer, the support layer capable of substantially conforming to an anatomical feature in the vertebral column of the patient, wherein the support layer holds the delivery layer in proximity to the anatomical feature; at least one rod; at least one rod clip; and at least one fastener.

In some embodiments, the rod clip comprises a first leg and a second leg. In some embodiments, the first and second legs are adapted to attach to the rod. In some embodiments, the rod clip further comprises an arm connected to the first and second legs by a stem. In some embodiments, the arm of the rod clip is positioned to apply pressure to the support layer of the multi-layer osteogenic carrier device to hold the multi-layer osteogenic carrier device in proximity to the anatomical feature.

In some embodiments, the rod clip is adapted to maintain pressure on the support layer of the multi-layer osteogenic carrier device. In some embodiments, the rod clip comprises at least one leg adapted to attach to the rod and an arm connected to the at least one leg. In some embodiments, the at least one leg is curved or curvilinear. In some embodiments, the at least one leg is connected to the arm by a stem. In some embodiments, the arm extends from the stabilization system to engage the support layer of the multi-layer osteogenic carrier device. In some embodiments, the fastener is inserted through the stem to lock the rod clip onto the rod once the clip has been placed in the desired position relative to the multi-layer osteogenic carrier device. In other embodiments, the spinal stabilization system comprises a plurality of rod clips and a plurality of multi-layer osteogenic carrier devices.

In some embodiments, the rod clip is inert or absorbable. In some embodiments, the rod clip attaches onto the rod dorsally. In other embodiments, the rod clip is bendable and is adapted to go over the multi-layer osteogenic carrier device and under the rod.

In some embodiments, the spinal stabilization system further comprises at least one pedicle screw. In some embodiments, the rod clip is attached to the at least one pedicle screw.

In some embodiments, the first leg and the second leg are configured to snap onto the rod and wrap around at least half of the circumference of the rod to attach to the rod clip. In some embodiments, the arm comprises a bent tip that is configured to press against the surface of the support layer. In some embodiments, the first leg and the second leg are configured to allow the rod clip to rotate and slide along the length of the rod, and wherein the fastener is configured to limit the degree of rotation and amount of slippage of the rod clip along the rod.

The carrier can be produced in one or more predetermined lengths in the form of an elongate, tubular, sleeve-like structure having a closed end and an open end for inserting the osteoinductive, osteogenic, and/or osteoconductive substance. The sleeve can be cut to the length needed (generally the inter-pedicular distance) and the osteoinductive, osteogenic, and/or osteoconductive substance placed within through the open end. After the substance is inserted, the open end can be sewn or clipped to prevent extrusion. Alternatively, the osteoinductive, osteogenic, and/or osteoconductive substance can be introduced into the carrier during production, and the carrier can be frozen or otherwise treated to preserve the viability and integrity of the substance. In such pre-filled embodiments, the carrier can be made in one or more predetermined sizes with both ends sealed, or in a pre-filled sleeve that can be cut to size, although it would result in loss of the osteoinductive substance at the ends during the cutting and sealing process. The segments can be combined longitudinally and held in place by the clips achieving a continuous contact with the decorticated bone.

The sleeves could come in different sizes depending upon the material and mass of the type material to be utilized; larger for a osteoconductive fusion matrix; smaller for the an osteoinductive substance or other agent alone and both larger and wider if the osteogenic and/or osteoconductive substance is to be mixed with autologous bone. The filled carrier could be placed in the appropriate position and be held in place by an inert or absorbable rod clip which fits onto a rod of a spinal stabilization system. This rod clip could attach onto the rod dorsally or could be bendable and go over the carrier and under the rod.

Exemplary embodiments of the carrier system and device as described are adapted to promote fusion between lumbar vertebrae in association with procedures such as posterior and posterior-lateral lumbar fusions and are especially designed to be used through minimally invasive approaches to the lumbar spine, although the embodiments can be used with standard open procedures or, with minor modifications, posterior cervical and thoracic fusions. The carrier is a single unit but has three distinct layers. The multi-layered carrier functions during insertion as a single unit so that it can be placed precisely, and is maintained in the desired anatomic position. Once positioned, rod clips can be placed over the device, holding it in place. The rod clips can be attached to rods and/or pedicle screws or another component of a spinal stabilization system. This would be true for both the three layered embodiment as well as a combination in which the first and second layers are combined and the third layer is initially a separate sheet or wafer which it placed above the first two layers.

In other embodiments, the carrier can be adapted for use in fusion procedures in the cervical spine. The carrier can be disc-shaped having an outer cylindrical wall defining a hollow inner chamber. The outer wall can be composed of a rigid, absorbable material capable of withstanding the axial loads in the cervical region. The outer wall can be composed of a material substantially similar to the third layer disposed above, although having substantially greater rigidity and structural integrity with a potential for remaining structurally sound for up to 6-12 months. Conceivably, this type of construct could be absorbed from the top and bottom edges progressively so that it allows the vertebral bodies to progressively place load sharing on the construct and thereby increasing the chance of obtaining a solid fusion in contract to fixed rigid cages which minimize load sharing and potentially shields the fusion material from forming solid bone.

A hollow core layer can be inserted into the center of the chamber. The core layer can be composed of the same of a material substantially similar to the second layer described. The carrier lumen can define a cavity for holding an osteoconductive, osteogenic, and/or osteoinductive substance as described above. The cavity can be pre-filled with an osteoinductive, osteogenic and/or osteoconductive substance, or the substance can be injected into the cavity through a port or inlet in the carrier.

Adherent plugs can be disposed on either side of the core layer at the top and bottom of the chamber. The plugs can be composed of the same or a substantially similar material to the first layer described above being adherent and osteoinductive. The carrier can be adapted for inserting between vertebrae in the cervical region of the spine to promote fusion.

The osteoconductive properties of the embodiments of the carrier and its ability to also reliably deliver an osteoinductive substance to a fusion site increases the consistency of bone formation and should increase the success rate for cervical surgeries. The embodiments of the carrier would also save a significant amount of time because it is largely self-contained, easily activated, and does not require a large amount of time on the part of the nurses and physician during the surgery to construct and apply. This should save both time and money, and be safer for the patient because it reduces operating room and anesthesia time. The embodiments of the carrier could be used for both open fusions and minimally invasive procedures.

Yet another aspect of the present invention comprises a method for providing an osteogenic material to a target site of the spine, comprising: providing a multi-layer osteogenic carrier device to the target site of the spine, the device comprising: a delivery layer comprising a porous material and an osteogenic material; and a support layer in communication with the delivery layer, the support layer capable of substantially conforming to an anatomical feature, wherein the support layer can hold the delivery layer in proximity to the anatomical feature. Such a method can further comprise stabilizing at least a portion of the spine with a spinal stabilization structure; and attaching the multi-layer osteogenic carrier device to the spinal stabilization structure using at least one rod clip. In an exemplary embodiment, a method for providing an osteogenic material to a target site can further comprise inducing osteogenesis at the target site of the spine.

BRIEF DESCRIPTION OF THE DRAWINGS

FIG. 3 illustrates a cross-sectional view of an exemplary embodiment of a rod clip.

DETAILED DESCRIPTION

Figure 1A:
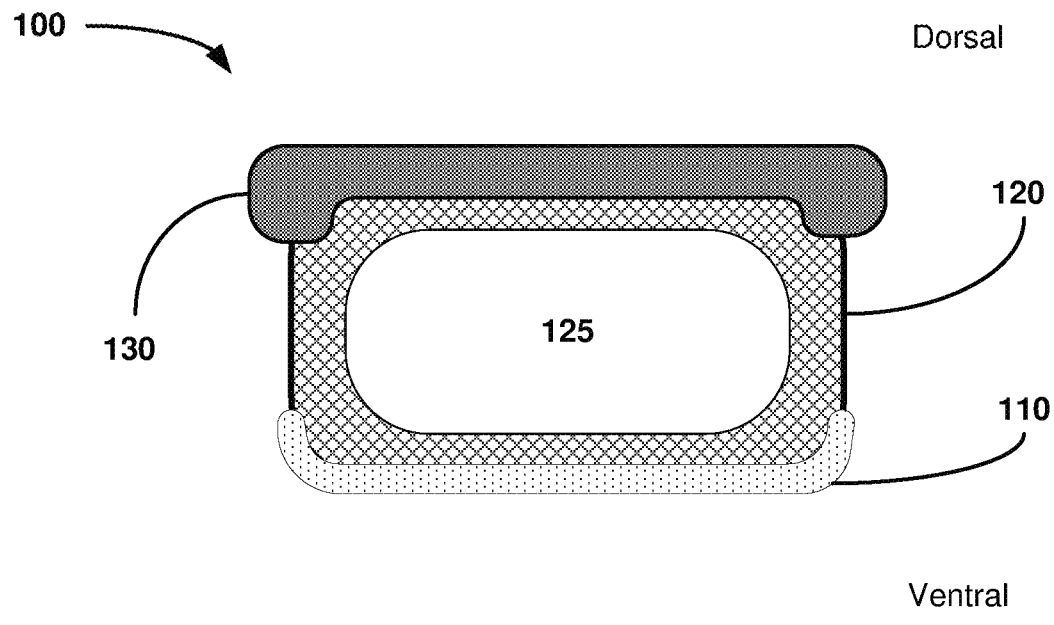
FIG. 1a illustrates an axial cross-sectional view of an exemplary embodiment of a carrier.

Referring now in detail to the Figures, wherein like reference numerals represent like parts throughout the several views, FIG. 1a illustrates an axial cross-sectional view of an exemplary embodiment of a carrier 100. The carrier 100 can comprise multiple layers serving distinct biologic functions and having different biologic properties. The layers can be composed of, able to stimulate, filled with, or impregnated with an osteogenic, osteoconductive, and/or osteoinductive substance and/or angiogenic factor.

As used herein, the term "osteogenic" refers to the development and formation of bone, which includes osteoinduction and osteoconduction. "Osteoinduction" or "osteoinductive" as used herein means facilitating, promoting, and/or inducing bone growth or formation. Stated another way, osteoinduction is the process of inducing osteogenesis. An osteoinductive substance or material as used herein refers to any substance, matrix, compound, material, or composition that facilitates, promotes, and/or induces bone growth or formation. Trinity™ and bone morphogenetic proteins are examples of osteoinductive substances. As used herein, the term "osteoconductive" or "osteoconduction" refers to any structure, material, device, matrix, or scaffold that facilitates the formation of bone structure. Trinity™ also has that property as do multiple other agents currently on the market such as Vitoss™. It is anticipated that newer agents will develop and the system described has the potential for use with multiple types of theoretical and actual biologics.

In an exemplary embodiment, the carrier 100 can be in the form of an elongate, tubular structure, which will be discussed further below. The carrier 100 can comprise a first layer 110, a second layer 120, and third layer 130. The second layer 120 can be disposed between the first layer 110 and the second layer 130.

The first layer 110 can be pliable and adherent to decorticated bone, and comprise the ventral or front side of the carrier 100. As such, the first layer 110 may be referred to as the adherent layer. When the carrier 100 is applied to a fusion site, the first layer 110 can be compressed onto the decorticated surface of the vertebrae where fusion is desired. The pliability and adherence of the first layer 110 enables the first layer 110 to substantially conform to the surface of the decorticated bone, maximizing the contact area between the bone and carrier 100, and prevent the carrier 100 drifting from the fusion site. The first layer 110 can have constant adherent properties, or alternatively, the first layer 110 can become adherent upon activation. The first layer 110 can be activated, for example and not limitation, by a fluid such as sterile saline, blood, or serum, or by another activating agent.

The first layer 110 can be constructed from an osteoinductive material optimally but alternative agents could conceivably be employed. In other contemplated embodiments, the first layer 110 can be able to stimulate or be impregnated or infused with an osteoinductive and/or angiogenic substance. The first layer 110 can be rapidly absorbed by the body. For example, it is preferable for the first layer 110 to be substantially absorbed relatively rapidly generally within 2-8 weeks although as biologics develop with shorter or longer durations, alternative absorptions rates are conceivable. For example only and not limitation, a material such as Infuse® containing Bone Morphogenetic Protein (rhBMP-2) exhibits substantially at least some of the properties preferred for the first layer 110. The first layer is preferably porous, absorbing blood or serum and allowing it to flow to the surface of the vertebrae to facilitate fusion.

The second layer 120 can compose the bulk of the carrier 100. The second layer 120 can define a hollow cavity 125 for receiving and holding an osteogenic, osteoconductive and/or osteoinductive substance and/or angiogenic factor. Accordingly, the second layer 120 may be referred to as the delivery layer. The second layer 120 can be thicker and be absorbed by the body slower than the first layer 110. For example only and not limitation, the second layer 120 can be preferably absorbed by the body in 26-52 weeks. The second layer can be porous, allowing blood or serum to seep into and intermix with the substance within the cavity 125, and for the substance to diffuse from the carrier 100 to the fusion site. The actual absorption time would be significantly dependent upon the in growth of the patient's own bone forming cells and vascularity. Once bone is formed by the patient the second layer is progressively absorbed and does not remain as an impediment to true bone formation.

The second layer 120 can be composed of an osteoconductive material or can have osteoconductive properties. The second layer 120 could additionally or alternatively be composed of an osteoinductive/osteogenic material or could have osteoinductive/osteogenic properties. The osteoconductive/osteoinductive properties of the second layer 120 combined with the osteoinductive properties of the substance disposed with the cavity 125 promote bone growth both within the second layer 120 itself and on the surface of the decorticated bone to facilitate fusion of vertebrae. Because the second layer is absorbent but is absorbed by the body slower than the first layer 110, it can be infiltrated by osteogenic cells from the body which would form the bone mass that would eventually extend to the decorticated surface facilitating fusion.

In alternative embodiments, the second layer 120 can be substantially uniform and not have a cavity 125 at its core. In such embodiments, an osteoinductive substance could be seeped or poured into the second layer 125, which would absorb and hold the substance like a sponge.

The third layer 130 can comprise the dorsal or back side of the carrier 100. The third layer 130 can in be communication with at least a portion of the second layer 120 (i.e., the delivery layer). As such, the third layer 130 can provide physical support to the delivery layer and may sometimes be referred to herein as a support layer. The third layer 130 can be rigid, substantially rigid, or may be moldable to a certain extent by the surgeon to form a variety of different shapes, contours, or configurations. For example, in some embodiments, the support layer is substantially rigid to achieve the desired effect. In other embodiments, the support layer is moldable to achieve the desired effect. The third layer 130 is preferably moldable by hand without special tools. The third layer 130 can be inherently or intrinsically moldable, or it can become moldable when activated. It may also be more rigid and in certain situations be able to achieve the same purpose. Thus, it is contemplated that moldability or rigidity of the support layer can be achieved by activating the support layer. For example and not limitation, the third layer 130 can be activated, by a fluid such as sterile saline, blood, or serum, or by another activating agent. Once the third layer 130 has been molded to a particular shape, it preferably retains that shape until it is remolded. The third layer could either be attached primarily to the other layers or could be a separate moldable layer that is cut to size, activated and then fits over the first two layers. In this last variation, the first and second layers could be of predetermined fixed lengths that are fitted to the defect and then held in place by the moldable third layer and the clips. When rigidity alone is sufficient, the clips may or may not be required to achieve the purpose of holding the first two layers in the optimal proximity.

The third layer 130 can hold the first layer 110 and second layer 120 in proximity to the decorticated bone and prevent them from becoming separated from the decorticated bone surface and lost within the surrounding muscle where they would be absorbed without any beneficial effect. The third layer 130 can be absorbed by the body at a substantially slower rate than the first layer 110 and second layer 120. For example only and not limitation, the third layer 130 can be preferably absorbed by the body in 26 weeks or longer. While the third layer 130 can be relatively dense and rigid compared to the first layer 110 and the second layer 120, it can allow bodily fluids to diffuse through it into the second layer 120 but preferably prevents the osteoinductive substance in the second layer from diffusing dorsally away from the fusion site where it would be absorbed by the body and effectively wasted.

The moldability and/or the rigid nature of the third layer 130 allow the carrier to conform to the surface contours of the bone at the fusion site and maximize the contact area between the carrier and fusion site. In embodiments having a moldable support layer, the surgeon can intraoperatively mold the third layer 130. The carrier 100 can be placed on the target fusion site, the third layer 130 can be pressed in the ventral direction so that the third layer 130 approximates and conforms to the shape of the fusion site while compressing the first layer 110 and second layer 120 against the decorticated bone.

The third layer 130 can interface with a spinal stabilization system to secure the carrier 100 to the fusion site. For example, one of more rod clips 300 (see FIG. 3) can be attached to rods of a spinal stabilization system, the rod clips 300 having an arm 340 that can press against the third layer 130 to secure the carrier 100 and prevent it from slipping or drifting out of place. Since the rod clips 300 can be attached anywhere on the rods, the carrier 100 can be optimally molded and placed to fit on a desired site on the vertebrae.

Figure 1B:
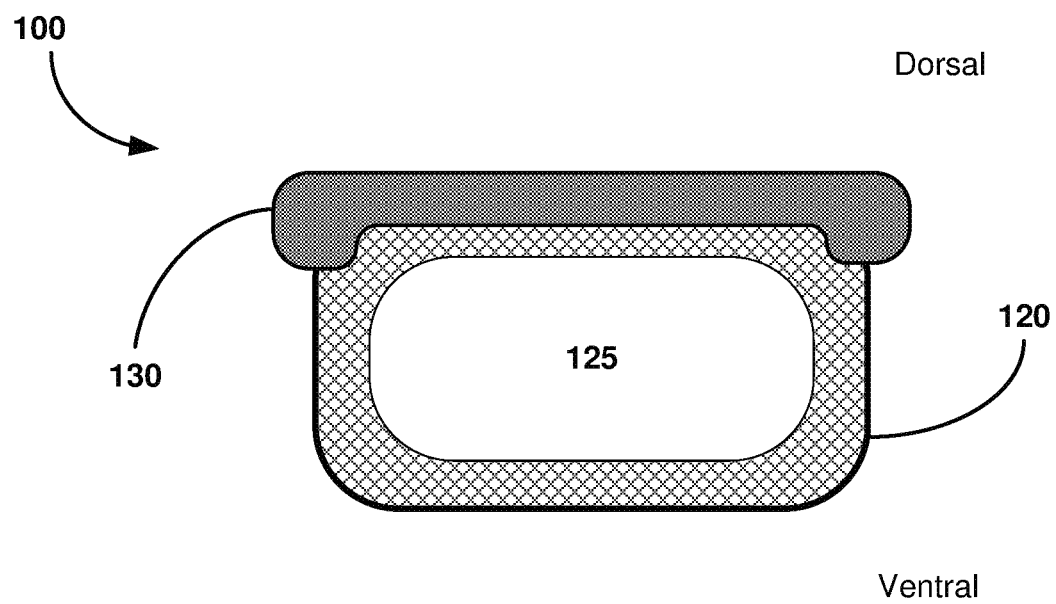
FIG. 1b illustrates a cross-sectional view of an alternative embodiment of a carrier.

FIG. 1b illustrates a cross-sectional view of an alternative embodiment of a carrier 100. In accordance with this and similar exemplary embodiments, the carrier 100 may not comprise a separate first layer 110. The properties and functionality of the first layer 110 can be incorporated into the second layer 120 or omitted. For example, the ventral surface of the second layer 120 can be adherent or have an adherent substance or component integrated into it. In other contemplated embodiments, the first layer 110 can be integrally formed into the second layer 120, rather than comprising a separate and distinct layer. In further contemplated embodiments, the first layer 110 could be omitted entirely.

Figure 1C:
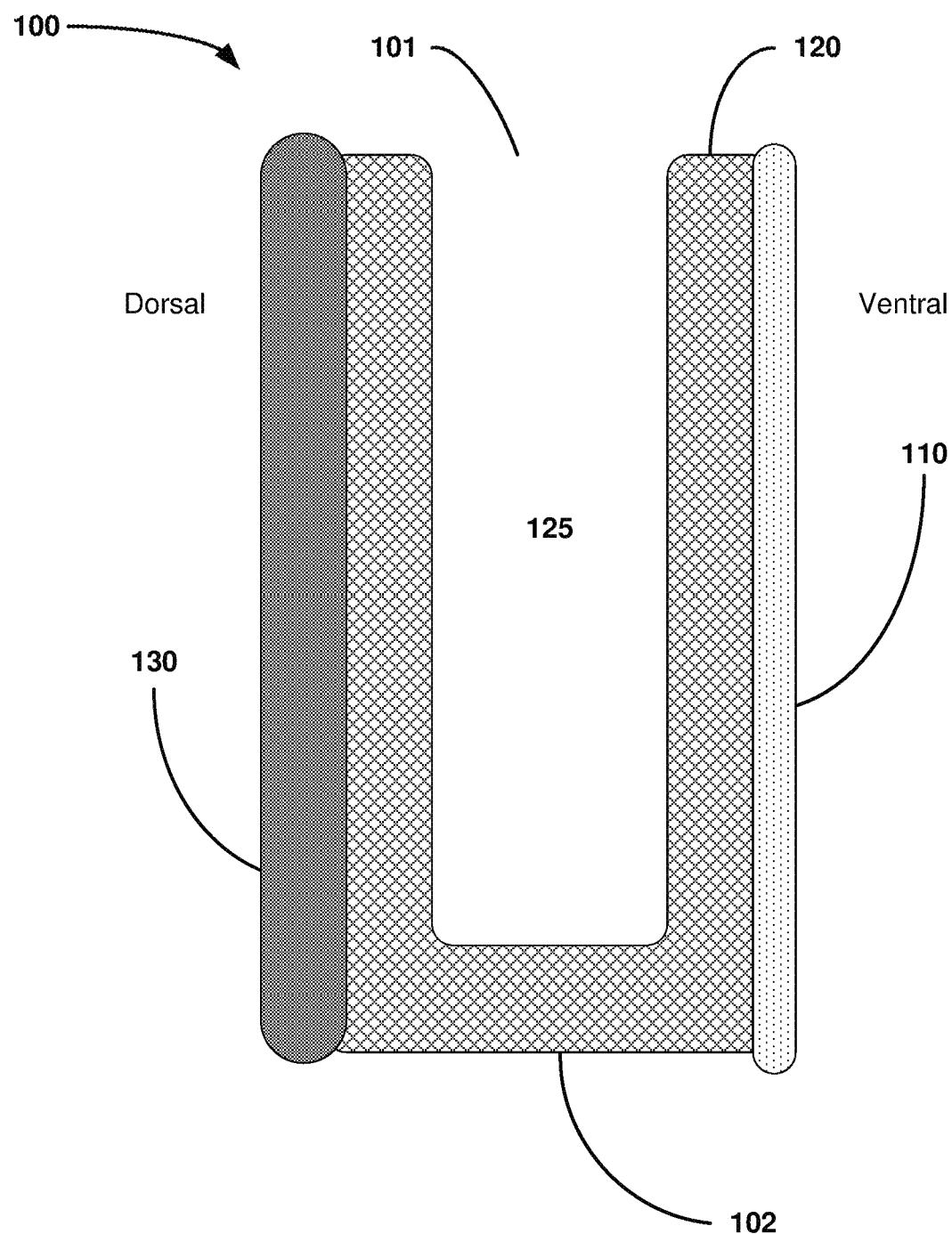
FIG. 1c illustrates a longitudinal cross-sectional view of an exemplary embodiment of a carrier.

Embodiments of carrier 100 can have a variety of different constructs. In an exemplary embodiment, the carrier 100 can take the form of an elongate, tubular sleeve-like construct. FIG. 1c illustrates a longitudinal cross-sectional view of an exemplary embodiment of a carrier 100 taking the form of such a construct. The carrier 100 can have a closed end 102 and an open end 101 for receiving an osteogenic, osteoinductive and/or osteoconductive substance. The carrier 100 can be produced in a variety of predetermined lengths, and be cut at the open end 101 to a desired length. The configuration of the carrier 100 having an open end 101 is desirable when the osteogenic, osteoconductive/osteoinductive substance must be frozen because the carrier can be dry packaged and shipped/stored separate from the substance until the time of surgery. The carrier 100 can be filled with the osteoconductive/osteoinductive substance by inserting the substance through the open end 101 into the cavity 125 and sealing the open end 101 with sutures or another absorbable fastening means or method.

In alternative embodiments, the carrier 100 can be produced in predetermined sizes with the osteoconductive/osteoinductive substance already sealed within the cavity 125. In such embodiments, the carrier 100 would not have an open end and would not be cut to a desired size. It could be of variable sizes that are longitudinally placed and held in place by the clips 300. In this configuration, the third layer could be separate and could be molded over the construct formed by the first two layers and held in place by the clips 300. Alternatively, the carrier 100 could have a port or inlet for injecting/inserting an osteoconductive/osteoinductive substance into the cavity 225.

Figure 2A:
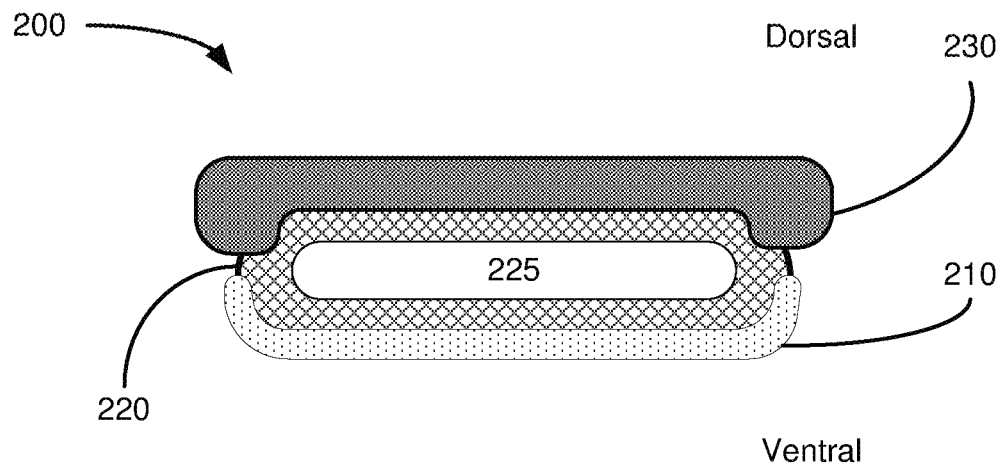
FIG. 2a illustrates an axial cross-sectional view of an exemplary embodiment of an empty/unpacked carrier.
Figure 2B:
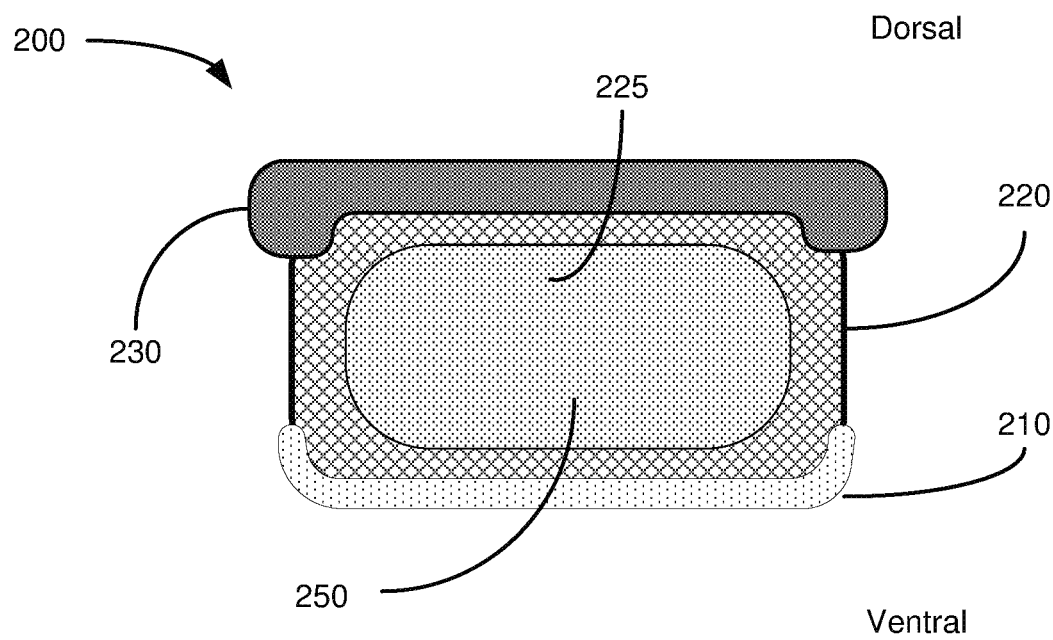
FIG. 2b illustrates an axial cross-sectional view of an exemplary embodiment of a filled/packed carrier.

FIG. 2a illustrates an axial cross-sectional view of an exemplary embodiment of an empty/unpacked carrier 100. The carrier 100 can be substantially thinner when the cavity 225 is empty. It allows for easier transport and storage. FIG. 2b illustrates an axial cross-sectional view of an exemplary embodiment of a filled/packed carrier 100. The carrier 100 can expand as an osteoconductive/osteoinductive substance 250 is packed or inserted into the cavity 225.

FIG. 3 illustrates a cross-sectional view of an exemplary embodiment of a rod clip 300. The rod clip 300 can attach to a rod 305 of a spinal stabilization system to secure a carrier 100 onto the decorticated bone and prevent the carrier 100 from being lifted off the fusion site. The rod clip 300 can also facilitate the fusion process by compressing the carrier 100 against the fusion site.

In an exemplary embodiment, the rod clip 300 can comprise a first leg 310 and a second leg 320. The first leg 310 and second leg 320 can be curvilinear and substantially follow the curvature of the rod 305. As the rod clip 300 is be pressed against the rod 305, the first leg 310 and second legs 320 can snap onto the rod 305 and wrap around at least half of the circumference of the rod 305 to attached to rod clip 300 to the rod 305.

A stem 330 can connect the first leg 310 and second leg 320 to an arm 340. The arm 340 can extend from the stem 330 and first leg 310 and second leg 320. The arm 340 can include a bent tip 350. The arm 340 can engage or otherwise interface with the third layer 130 of the carrier 100. In particular, the carrier 100 can be compressed onto the fusion site by rotating the rod clip 300 around the rod 305 such that the arm 340 presses against the third layer 130. The bent tip 350 can provide press into the surface of the third layer 130 for additional grip or prevent the carrier 100 from sliding in the longitudinal direction along the length of the arm 340.

The rod clip 300 can include a fastener for fastening 360 the rod clip 300 to the rod 305. The legs 310 and 320 secure the rod clip 300 to the rod 305, but allow for a degree of rotation and sliding along the length of the rod 305. The fastening means 360 can secure the rod clip 300 to the rod 305 to limit the rotation and slippage of the rod clip 300. The fastening means 360 can be a mechanical fastener, such as a screw or bolt, or can be an adhesive, magnet, or other fixation element, mechanism or device.

Figure 4A:
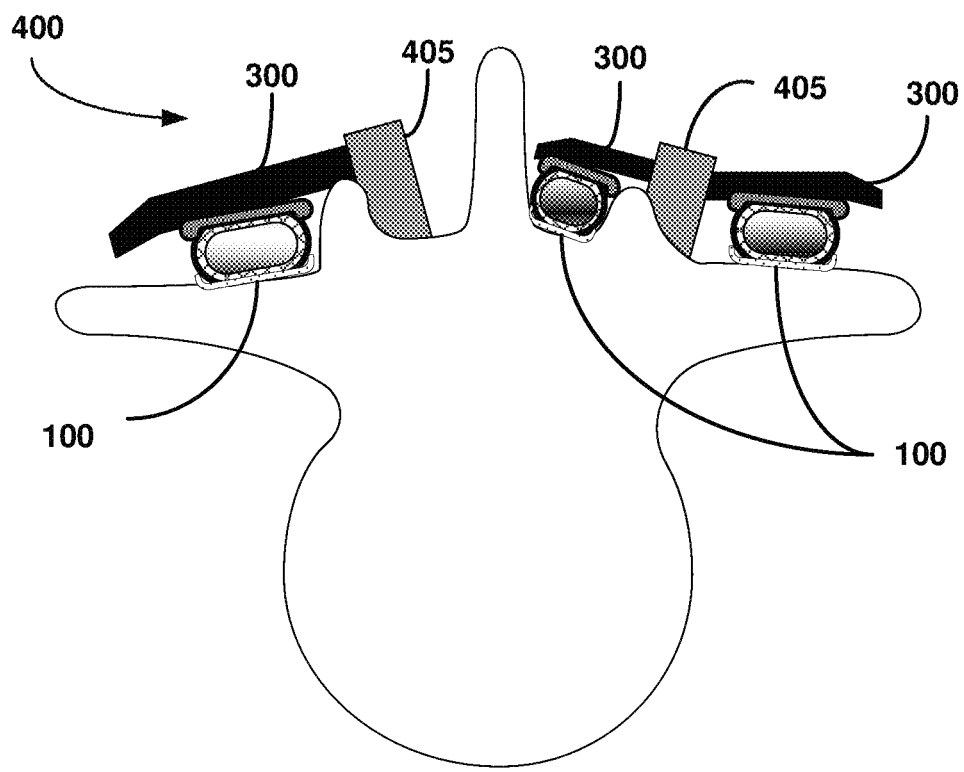
FIG. 4a illustrates a cross-sectional view in the transverse plane of exemplary embodiments of a carrier and system for applying the carrier on the transverse process and lamina.
Figure 4B:
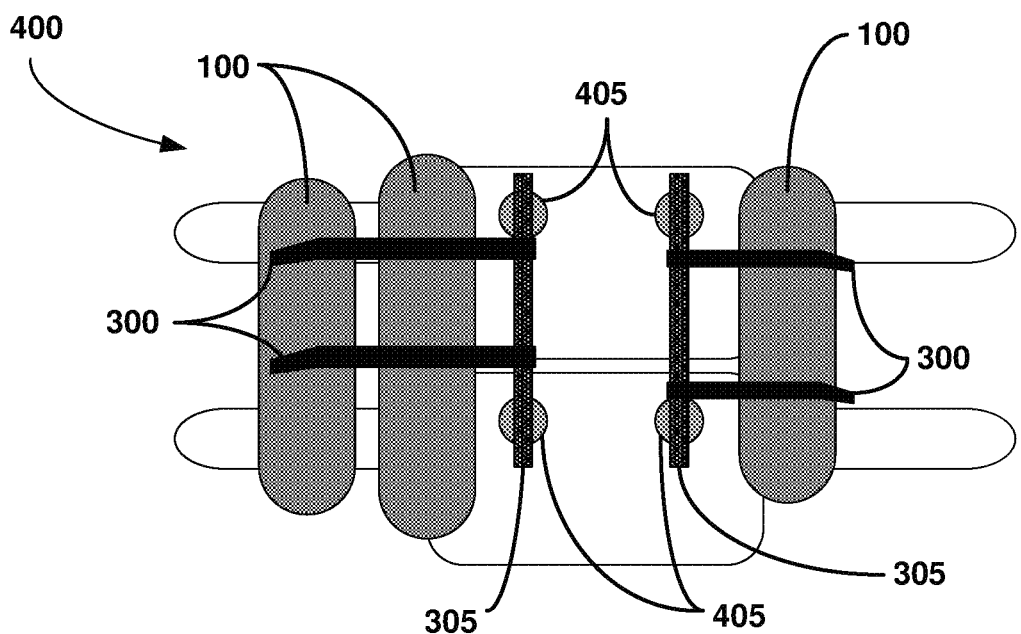
FIG. 4b illustrates a view in the coronal plane of a carrier and system for applying the carrier on the posterior surface.

FIG. 4a illustrates a cross-sectional view in the transverse plane of exemplary embodiments of a carrier 100 and system 400 for applying the carrier on the transverse process and lamina. The system 400 can comprise a spinal stabilization structure having pedicle screws 405 on adjacent vertebrae connected by a plurality of rods 305. A plurality of rod clips 300 can be attached to the rods 305 to keep a plurality of carriers 100 compressed on the decorticated bone of the target site. As used herein, the term "plurality" refers to more than one. FIG. 4b illustrates a view in the coronal plane of a carrier 100 and system 400 for applying the carrier 100 on the posterior surface of the vertebral column. In contemplated embodiments, the system 400 can comprise different spinal stabilization structures such as cages, structural allografts, interbody devices, and devices designed to be placed between and/or attached to the spinous processes, the vertebral bodies or onto and/or through the facets.

Figure 5:
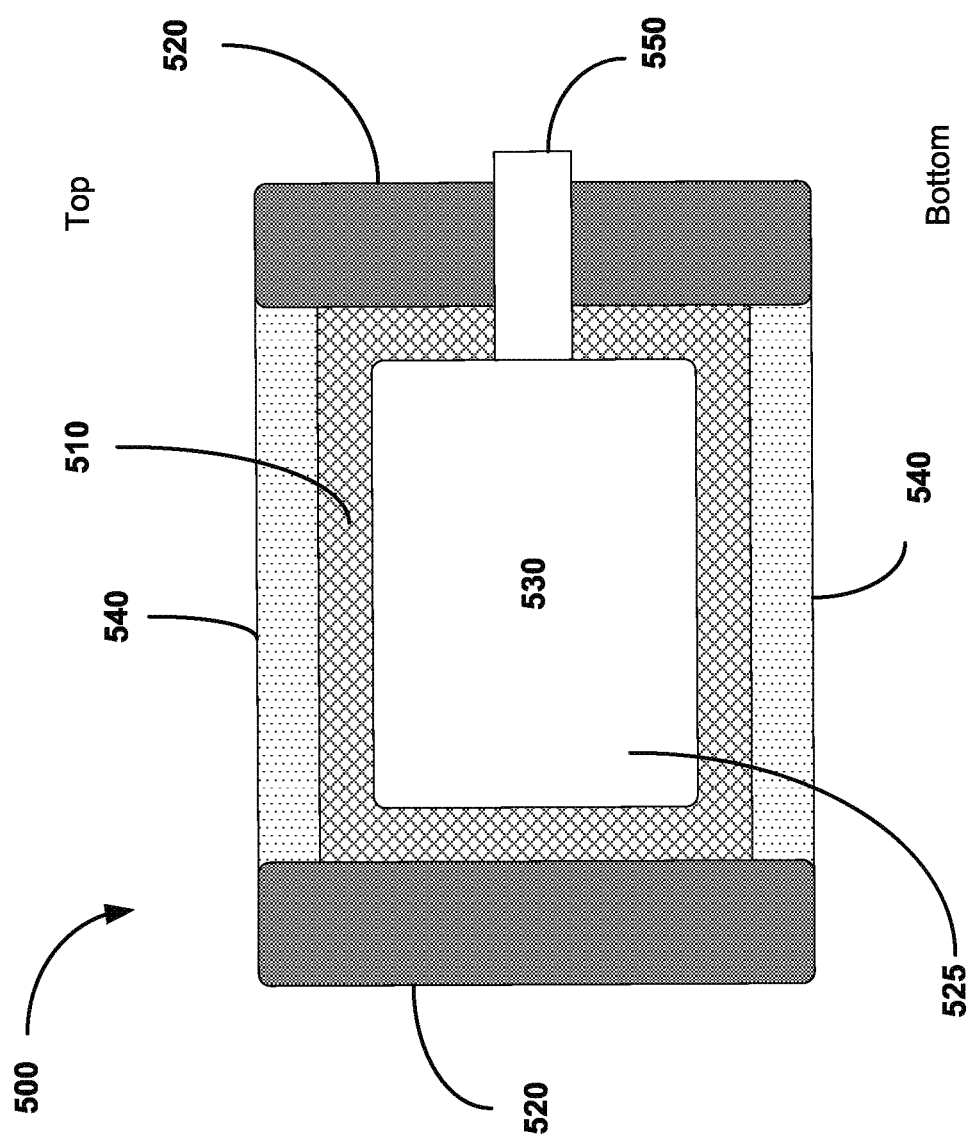
FIG. 5 illustrates an exemplary embodiment of a carrier adapted for use in the cervical region of the vertebral column.

FIG. 5 illustrates an exemplary embodiment of a carrier 500 adapted for use in the cervical region of the vertebral column. The carrier 500 can have similar properties to the carrier 100, but is specifically adapted for insertion between vertebrae to facilitate fusion rather than for placement on the surface of vertebrae like carrier 100. The carrier 500 can be particularly adapted for insertion between the vertebrae of the cervical region of the vertebral column but in a larger form could also be used between the thoracic or lumbar bodies.

The carrier 500 can comprise a hollow cylindrical wall 520 defining an inner chamber 525. The wall 520 can be composed of a biocompatible material that is substantially rigid and capable of withstanding the axial forces in the cervical, thoracic or lumbar region of the vertebral column. In particular, when the carrier 500 is inserted between vertebrae in the cervical region, it will experience forces in downward and upward directions as the adjacent vertebrae compress the carrier 500. The carrier 500 preferably has sufficient structural integrity and rigidity to sustain these forces without buckling, cracking, or otherwise being structurally compromised. The wall 520 of the carrier 500 could be designed to be absorbed in a fashion which allows progressive load sharing as the fusion mass becomes more mature and more capable of withstanding axial loading.

The cylindrical wall 520 can be composed of material absorbable by the body. The wall 520 preferably is absorbed at a substantially slower rate than the other components of the carrier 500. Preferably, the wall 500 does not dissolve before the vertebrae are fused and are capable of sustaining axial loads present in the cervical spine unassisted. For example and not limitation, the wall 520 can be substantially absorbed by the body within 6-24 months. Within the cervical spine, settling is generally assumed to take place with six months although data suggests this process may continue over an even longer time period.

A core layer 510 can be disposed within the chamber 525. The core layer 510 can be substantially similar in functionality, properties, and attributes to the second layer 120 described above. The core layer 510 can define a cavity 530 for receiving an osteoinductive/osteoconductive substance. The cavity 530 can be pre-filed during the manufacturing process or can be filled prior to surgery by injecting the substance through a port 550 spanning the wall 520 and core layer 510.

Chamber plugs 540 can seal the top and bottom portions of the chamber 525. The plugs 540 can be substantially similar in functionality, properties, and attributes to the first layer 110 described above. The wall 520 and plugs 540 can substantially surround the core layer 510. Once inserted between vertebrae, the carrier 500 can promote fusion as the plugs 540 dissolve and bone growth occurs in and around the core layer 510. After a period of time, the entire chamber 525 may be filled with fused bone and the wall 520 will be absorbed by the body and also replaced with fused bone.

The various embodiments described above are intended to provide a carrier device, system for facilitating vertebral fusion, and a method of using and making said system and device. Consequently, the embodiments described above are merely exemplary and not limiting. In particular, the configurations, dimensions, orientation, inter-relationships, properties, attributes, and functionalities of elements described above can be modified from what has been recited and described without departing from the design of the invention.

What is claimed is:

1. A spinal stabilization system for use in a vertebral column of a patient, comprising:
   a multi-layer osteogenic carrier device comprising:
      a delivery layer comprising a porous material and an osteogenic material; and
      a support layer in communication with the delivery layer, the support layer capable of substantially conforming to an anatomical feature in the vertebral column of the patient,
      wherein the support layer holds the delivery layer in proximity to the anatomical feature;
   at least one rod;
   at least one rod clip; and
   at least one fastener,
   wherein the at least one rod clip comprises:
      a first leg and a second leg that are adapted to attach to the at least one rod;
      a stem having a first side and a second side located opposite the first side, the stem projecting upward from the rod;
      and an arm directly connected to the stem at the second side,
      wherein the first side of the stem is directly connected to each of the first leg and the second leg and is located proximal the rod,
      wherein the fastener passes through the stem from the second side to the first side, and
      wherein the arm is substantially perpendicular to the at least one rod.

2. The spinal stabilization system of claim 1, wherein the arm of the at least one rod clip is positioned to apply pressure to the support layer of the multi-layer osteogenic carrier device to hold the multi-layer osteogenic carrier device in proximity to the anatomical feature.

3. The spinal stabilization system of claim 1, wherein the at least one rod clip is adapted to maintain pressure on the support layer of the multi-layer osteogenic carrier device.

4. The spinal stabilization system of claim 1, wherein at least one of the first leg and the second leg is curved or curvilinear.

5. The spinal stabilization system of claim 4, wherein at least one of the first leg and the second leg is connected to the arm by the stem.

6. The spinal stabilization system of claim 5, wherein the arm extends from the stabilization system to engage the support layer of the multi-layer osteogenic carrier device.

7. The spinal stabilization system of claim 6, wherein the at least one fastener is inserted through the stem to lock the at least one rod clip onto the at least one rod once the clip has been placed in the desired position relative to the multi-layer osteogenic carrier device.

8. The spinal stabilization system of claim 6, wherein the spinal stabilization system comprises a plurality of rod clips and a plurality of multi-layer osteogenic carrier devices.

9. The spinal stabilization system of claim 4, wherein the first leg and the second leg are configured to snap onto the at least one rod and wrap around at least half of the circumference of the at least one rod to attach to the at least one rod clip.

10. The spinal stabilization system of claim 9, wherein the arm comprises a bent tip that is configured to press against the surface of the support layer.

11. The spinal stabilization system of claim 10, wherein the first leg and the second leg are configured to allow the at least one rod clip to rotate and slide along the length of the at least one rod, and wherein the fastener is configured to limit the degree of rotation and amount of slippage of the at least one rod clip along the at least one rod.

12. The spinal stabilization system of claim 1, wherein the at least one rod clip is inert or absorbable.

13. The spinal stabilization system of claim 12, wherein the at least one rod clip attaches onto the at least one rod dorsally.

14. The spinal stabilization system of claim 12, wherein the at least one rod clip is bendable and is adapted to go over the multi-layer osteogenic carrier device and under the at least one rod.

15. The spinal stabilization system of claim 12, wherein the at least one rod clip is attached to at least one of the pedicle screws.

16. The spinal stabilization system of claim 1, further comprising at least two pedicle screws.

17. The spinal stabilization system of claim 1, wherein the arm is adapted to extend outward from a spinous process of the vertebra to a transverse process of the vertebra.

* * * * *